US00PP14953P2

(12) United States Plant Patent
Beckmann

(10) Patent No.: US PP14,953 P2
(45) Date of Patent: Jun. 29, 2004

(54) BEGONIA PLANT NAMED 'CAROLINE'

(50) Latin Name: *Begonia×hybrida*
Varietal Denomination: Caroline

(76) Inventor: Rudolf Beckmann, Gartnersiedlung 16, 24610 Gönnebek (DE)

( * ) Notice: Subject to any disclaimer, the term of this patent is extended or adjusted under 35 U.S.C. 154(b) by 0 days.

(21) Appl. No.: 10/637,065

(22) Filed: Aug. 7, 2003

(51) Int. Cl.[7] ..... A01H 5/00

(52) U.S. Cl. ..... Plt./348

(58) Field of Search ..... Plt./348

*Primary Examiner*—Anne Marie Grunberg
*Assistant Examiner*—Susan B. McCormick-Ewoldt
(74) *Attorney, Agent, or Firm*—C. A. Whealy

(57) ABSTRACT

A new and distinct cultivar of Begonia plant named 'Caroline', characterized by its compact, upright and rounded plant habit; double flowers that are light red purple in color and held above and beyond the foliage; and excellent postproduction longevity.

1 Drawing Sheet

Botanical classification/cultivar designation: *Begonia× hybrida* cultivar Caroline.

BACKGROUND OF THE INVENTION

The present Invention relates to a new and distinct cultivar of Begonia plant, botanically known as *Begonia× hiemalis*, commercially known as Elatior Begonia, and hereinafter referred to by the name 'Caroline'.

The new Begonia was discovered by the Inventor in a controlled environment in Gönnebek, Germany, in 2001, as a naturally-occurring whole plant mutation of *Begonia× hiemalis*, 'Kaya', disclosed in a U.S. Plant patent application Ser. No. 10/637,059 filed concurrently. The new Begonia was observed as a single flowering plant within a population of flowering plants of the cultivar Kaya. The selection of this plant was based on its unique flower coloration.

Asexual reproduction of the new Begonia by cuttings taken in a controlled environment in Gönnebek, Germany, since 2001 has shown that the unique features of this new Begonia are stable and reproduced true to type in successive generations.

SUMMARY OF THE INVENTION

The cultivar 'Caroline' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Caroline'. These characteristics in combination distinguish 'Caroline' as a new and distinct Begonia cultivar:

1. Compact, upright and rounded plant habit.
2. Freely branching growth habit.
3. Double flowers that are light red purple in color and held above and beyond the foliage.
4. Excellent postproduction longevity.

Plants of the new Begonia are most similar to plants of the present cultivar Kaya; however plants of the new Begonia differ from plants of the cultivar Kaya primarily in flower color as plants of the cultivar Kaya have light pink-colored flowers.

BRIEF DESCRIPTION OF THE PHOTOGRAPHS

The accompanying colored photographs illustrate the overall appearance of the new Begonia, showing the colors as true as it is reasonably possible to obtain in colored reproductions of this type. Colors in the photographs may differ slightly from the color values cited in the detailed botanical description which accurately describe the colors of the new Begonia.

The photograph at the top of the sheet comprises a side perspective view of a typical flowering plant of 'Caroline'.

The photograph at the bottom of the sheet is a close-up view of typical flowers and leaves of 'Caroline'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Gönnebek, Germany, under commercial practice during the summer in a glass-covered greenhouse. During the production of the plants, day temperatures were about 20° C., night temperatures were about 19° C., and light levels were about 3,000 kilolux. After planting rooted cuttings into 12-cm containers, one week of long nyctoperiods of 16 hours was given followed by short nyctoperiods of eight hours until flowering. Plants were about three months old when the photographs and description were taken. Measurements and numerical values represent averages for typical flowering plants.

Botanical classification: *Begonia×hiemalis* cultivar Caroline.

Commercial classification: Elatior Begonia.

Parentage: Naturally-occurring whole plant mutation of *Begonia×hiemalis* cultivar Kaya, disclosed in a U.S. Plant Patent application filed concurrently.

Propagation:

*Type.*—Cuttings.

*Time to initiate roots.*—About 21 days at temperatures of 20° C.

*Time to develop roots.*—About 35 days at temperatures of 20° C.

*Root description.*—Fibrous, well-branched, dense. Plants of the new Begonia have not been observed to form tubers.

Plant description:

*Plant form.*—Compact, upright and rounded plant habit; mounded inverted triangle; freely branching with good stem and stem base strength. Flowers are double and abundant.

*Growth habit.*—Moderate growth rate, vigorous. Suitable for 11 to 15-cm containers. Vegetative shoots are formed at basal nodes and flowering shoots are formed at upper nodes.

*Plant height.*—About 23 to 27 cm.

*Plant width.*—About 32 cm.

*Leaves.*—Arrangement: Simple, alternate. Developing leaves, length: About 9 to 10 cm. Developing leaves, width: About 6 to 8 cm. Fully expanded leaves, length: About 13 to 16 cm. Fully expanded leaves, width: About 10 to 13 cm. Shape: Asymmetrical, more or less reniform. Apex: Acuminate. Base: Cordate. Margin: Doubly serrate. Texture: Glabrous. Venation pattern: Palmate. Color: Developing and fully expanded leaves, upper surface: 147A. Developing and fully expanded leaves, lower surface: 148D overlain with 182A. Venation, upper and lower surfaces: 146D. Petiole length: About 4 to 8 cm. Petiole texture, upper and lower surfaces: Pubescent. Petiole color, upper and lower surfaces: Lighter than 146D.

Flower description:

*Flowering habit.*—Double flowers with numerous tepals arranged in axillary cymes. Usually two to six flowers per cyme. Many cymes in flower simultaneously. Flowers positioned above and beyond the foliage.

*Natural flowering season.*—Plants will flower year around regardless of nyctoperiod, however plants flower earlier and more abundantly from mid-February until November in the Northern Hemisphere. Flowering continuous.

*Postproduction longevity.*—Plants will maintain good flower and leaf substance for about 90 days in an interior environment.

*Flowers.*—Shape: Rounded. Diameter: About 5 to 7 cm. Depth (height): About 1.5 cm.

*Flower buds.*—Length: About 1 to 1.2 cm. Diameter: About 7 to 9 mm. Color: 60B.

*Tepals.*—Arrangement: Rosette. Quantity per flower: Usually about 25 per flower. Shape: Obovate. Apex: Rounded. Margin: Mostly entire to slightly crenate. Size, outer tepals: Length: About 2.2 to 2.6 cm. Width: About 2 to 2.3 cm. Size, inner tepals: Length: About 0.7 to 1.2 cm. Width: About 0.8 to 1 cm. Texture: Smooth, glabrous; satiny. Color: When opening, upper and lower surfaces: 9A. Fully opened, upper surface: 68C. Fully opened, lower surface: 55B to 55D.

*Flower bracts.*—Arrangement: Two, opposite. Shape: Cordate. Apex: Acute. Margin: Slightly serrate. Texture: Smooth, glabrous. Color, upper and lower surfaces: 144B.

*Peduncles.*—Angle: Erect. Length: About 3.5 to 5.5 cm. Texture: Slightly pubescent. Color: Between 144C and 146D.

*Pedicels.*—Angle: Slightly bent. Length: About 1 to 3 cm. Texture: Glabrous. Color: Close to 151A.

*Reproductive organs.*—Stamens: None observed. Pistils: None observed.

*Seed/fruit.*—Seed and fruit production has not been observed as reproductive organs are not formed.

Disease/pest resistance: Plants of the new Begonia have not been observed to be resistant to pathogens and pests common to Begonias.

Temperature tolerance: Plants of the new Begonia have been observed to tolerate temperatures from 14 to 35° C.

It is claimed:

1. A new and distinct cultivar of Begonia plant named 'Caroline', as illustrated and described.

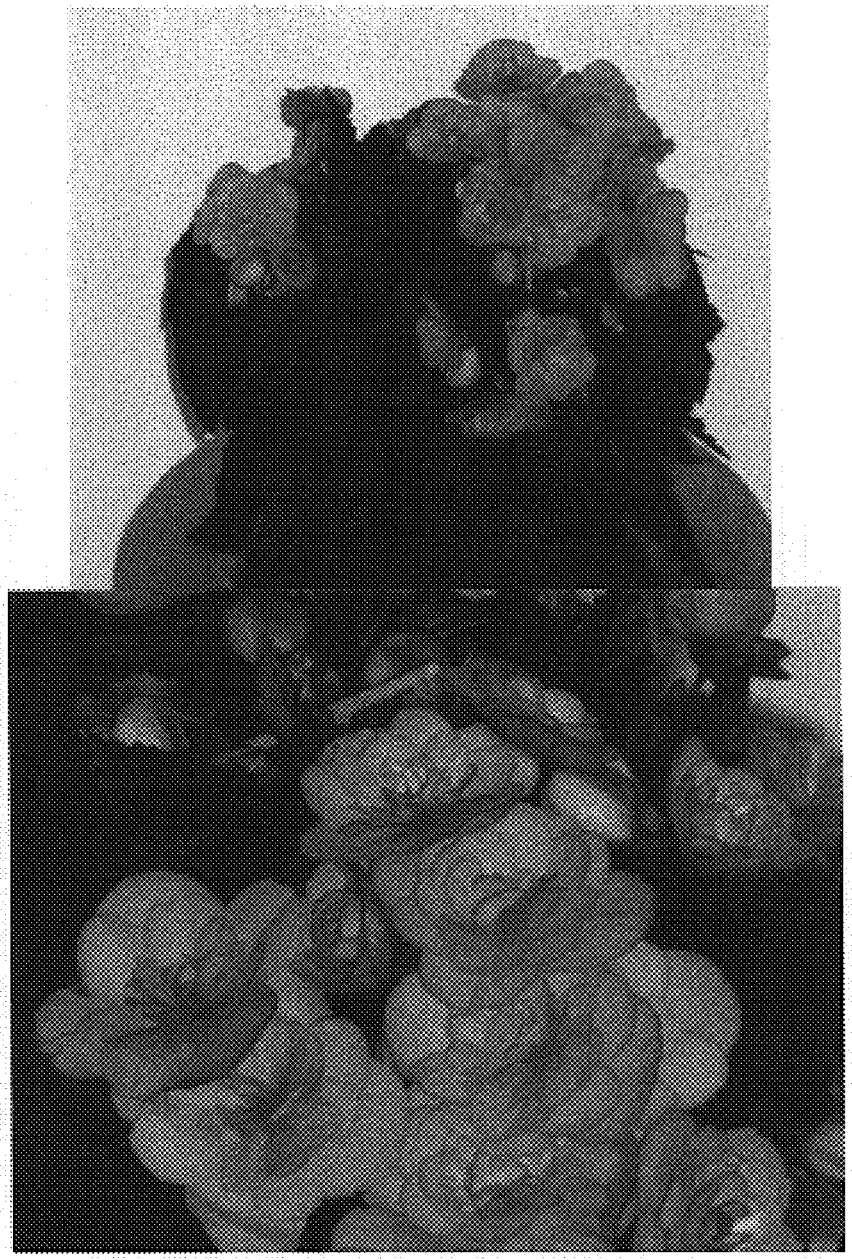

* * * * *